United States Patent [19]

Oliver

[11] 4,354,486
[45] Oct. 19, 1982

[54] OVERHEAD TABLE DRAPE

[75] Inventor: Don W. Oliver, Memphis, Tenn.

[73] Assignee: The Buckeye Cellulose Corporation, Cincinnati, Ohio

[21] Appl. No.: 192,136

[22] Filed: Sep. 29, 1980

[51] Int. Cl.³ ............................................. A61F 13/00
[52] U.S. Cl. ................................................. 128/132 D
[58] Field of Search .................................... 128/132 D

[56] References Cited

U.S. PATENT DOCUMENTS

| | | | |
|---|---|---|---|
| 3,537,446 | 11/1970 | Rowland et al. | 128/132 D |
| 3,910,268 | 10/1975 | Miller | 128/132 D |
| 3,926,185 | 12/1975 | Krzewinski | 128/132 D |
| 3,930,497 | 1/1976 | Krebs et al. | 128/132 D |
| 3,998,221 | 12/1976 | Collins | 128/132 D |
| 4,164,941 | 8/1979 | Knopick et al. | 128/132 D |

*Primary Examiner*—Michael H. Thaler
*Attorney, Agent, or Firm*—Milton B. Graff, IV; John V. Gorman; Richard C. Witte

[57] ABSTRACT

Described herein is a drape for covering an overhead table. The drape includes a doubled flap connected to the underside of each of a first pair of juxtaposed stacks of panels made by folds around parallel fold lines, in turn shortened transversely from each end to form a second pair of stacks of panels. The folded drape is positioned adjacent a reference edge of the table to be draped, and transversely unfolded so that the fold lines of each stack of the first pair of stacks are parallel to the table edge. The reference edge is covered, preparatory to positioning of the table, by the doubled flap which is folded atop one of first pair of stacks. The edges other than the reference edge can then be draped by unfolding one of the stacks of panels to cover them. The flap is held in position hanging over the reference edge of the table by the weight of the unfolded stack of panels above the flap and by the rest of the drape. The table can then be positioned over the patient and the stack of panels which retains the flap in position, and thus the flap as well, pulled down onto the patient.

14 Claims, 14 Drawing Figures

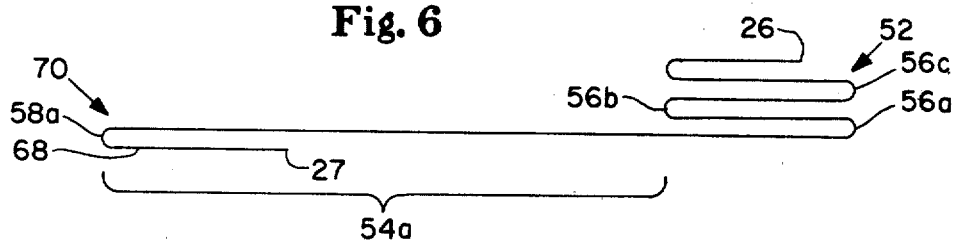
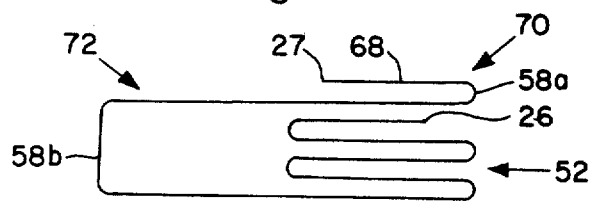
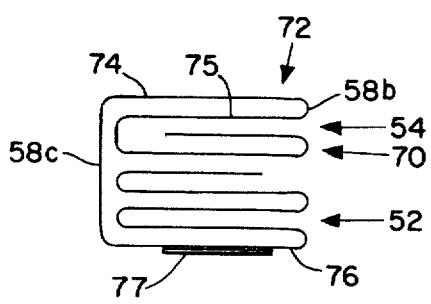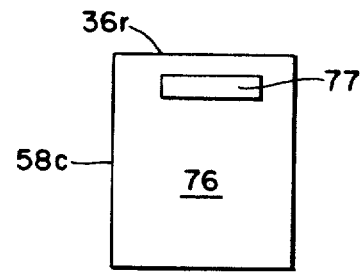

OVERHEAD TABLE DRAPE

TECHNICAL FIELD

This invention relates to a table drape for use in a surgical operating room and, more specifically, to a drape for an overhead or straddling-type table therein.

BACKGROUND ART

In the past, overhead tables in operating rooms have been draped preparatory to positioning over a patient by unfolding a drape to cover three edges of the table and maintaining at least one stack of folded panels of the drape in a position to cover the fourth edge of the table. The table is then positioned over the patient and the fourth stack of panels pulled down onto the patient. Such a draping procedure is described in U.S. Pat. No. 3,998,221 issued on Dec. 21, 1976 to Collins which uses two drapes to cover the table. A short set up drape is first unfolded over the reference edge of the table, which is the edge placed next to the operative site. The table drape is then unfolded over the set up drape covering the three edges of the table other than the reference edge. The reference edge of the table, covered by the set up drape, is not covered by the table drape until after the table is positioned over the patient. A stack of folded table drape panels positioned adjacent to the reference edge is then pulled over the reference edge and down onto the patient.

Another drape for surgical tables is disclosed in U.S. Pat. No. 4,164,941 issued to Knopick et al. on Aug. 21, 1979. A rectangular drape is folded inwardly from each of two opposed edges to form a drape shortened in one dimension; the shortened drape subsequently is shortened in a perpendicular direction by folding inwardly from each of the remaining opposed edges, creating four stacks of panels. A folded sheet of material is adhesively attached to the drape near one edge. The table can be covered by unfolding the four stacks of panels while retaining the attached sheet in position until needed. The sheet, positioned inside the folded drape, is draped down over the reference edge of the table extending below the adjacent edge of the drape after the remainder of the drape has been unfolded.

It is an object of this invention to provide an overhead table drape which can be economically produced and easily used. It is still another object of this invention to provide an overhead table drape which is a single sheet of material and which requires that only one sheet of material be used to drape the table and to protect the reference edge of that table while the drape is being unfolded and the table is being positioned over the patient.

DISCLOSURE OF THE INVENTION

This invention relates to a folded overhead table drape. The drape comprises a pair of stacks of panels which are folded around parallel fold lines. The pair of stacks is connected by a length of material which is folded on top of the stacks.

BRIEF DESCRIPTION OF THE DRAWINGS

FIGS. 6 and 7 are enlarged cross-sectional views showing transverse folding of the laterally folded drape.

FIG. 8 is an enlarged cross-sectional view of the transversely folded drape.

FIG. 9 is a bottom plan view of the folded drape shown in cross-section in FIG. 8.

It should be noted with respect to FIGS. 2 through 4 and 6 through 8, that the dimensions of the folds, stacks, etc., are exaggerated for clarity of the folded structure.

DETAILED DESCRIPTION OF THE INVENTION

Figure 1:
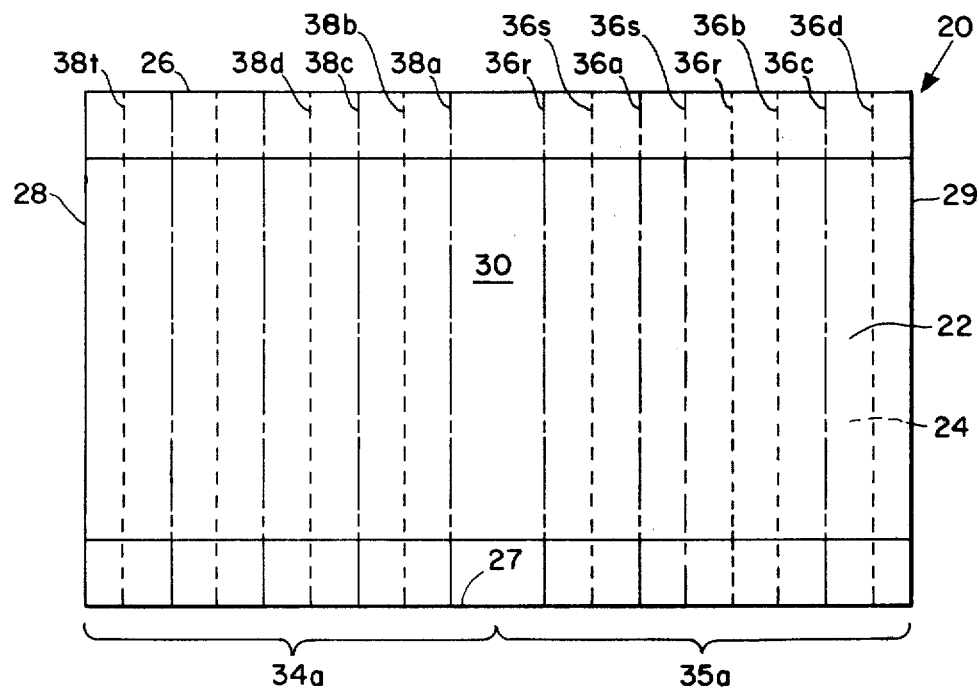
FIG. 1 is a plan view of the drape before folding.

Referring to the drawings wherein like reference characters are utilized to identify like parts throughout the several views, there is illustrated in FIG. 1 a reinforced, rectangular overhead table drape 20. In a preferred embodiment, the drape 20 is made up of a layer of thin polymeric film, preferably embossed polyethylene conveniently about 4 mils thick. The drape 20, shown in FIG. 1 has upper side 22, lower side 24, a pair of opposed longitudinal edges 26 and 27 and a pair of opposed lateral edges 28 and 29.

Preferably a reinforcing layer 30 is attached adhesively to the upper side 22 of the drape 20. The layer 30 may be any strong nonwoven fabric such as the laminated tissue and nonwoven fabric described in U.S. Pat. No. 4,113,911 issued to LaFitte et al. on Sept. 12, 1978. The layer 30 extends from one lateral edge 28 of the drape to the opposed lateral edge 29, spaced inwardly from both longitudinal edges 26 and 27 of the drape. Preferably the layer 30 is of a size sufficient to cover the top of the table to be draped and extend at least a short distance over the table edges to reinforce these heavily stressed areas. The layer 30 can conveniently be secured by a plurality of spaced longitudinal glue lines (not shown). To cover a standard Gerhardt or Phelan table a drape with lateral edges 28 and 29 of about 180 centimeters and longitudinal edges 26 and 27 of about 230 centimeters is convenient with layer 30 conveniently measuring about 135 centimeters by about 230 centimeters centered between the longitudinal edges 26 and 27 of the drape.

Figure 5:
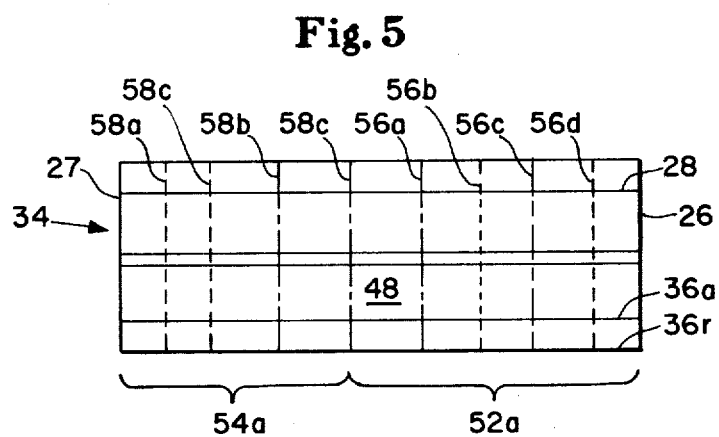
FIG. 5 is a plan view of the laterally folded drape before transverse folding.

As used herein with reference to FIG. 1, the term "forward fold" refers to a fold which brings upper side 22 surfaces together while the term "reverse fold" as used herein is a fold which results in bringing lower side 24 surfaces together. Similarly, with reference to FIG. 5, a "forward fold" refers to a fold which brings the upper side surfaces pictured therein together and a "reverse fold" brings the lower side surfaces together. The term "fan fold" as used herein refers to a folding pattern which is the result of alternating forward and reverse folds. The term "roll fold" as used herein refers to a folding procedure involving folding a doubled length of material upon itself. In FIGS. 1 and 5 a forward fold line is indicated by a dashed line made up of long and short segments while a reverse fold line is indicated by a dashed line made up of segments of equal length.

Figure 2:
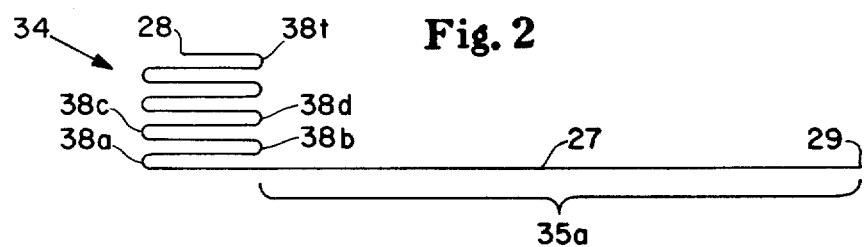
FIGS. 2 and 3 are enlarged cross-sectional views of the drape in the process of being folded laterally.
Figure 3:
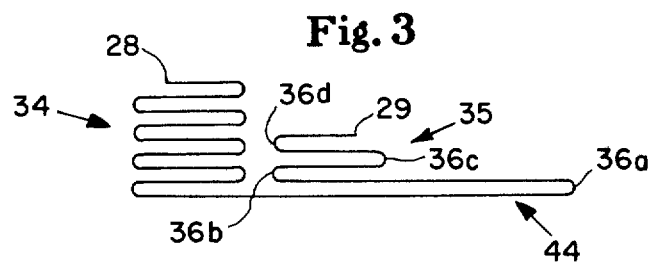
Figure 4:
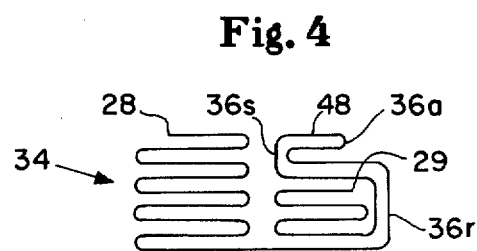
FIG. 4 is an enlarged cross-sectional view of the drape which has been laterally folded.

Referring to FIGS. 2, 3 and 4, two juxtaposed stacks 34 and 35 of lateral panels are formed by fan folding the opposed lateral edges 28 and 29 inwardly towards the center of the drape. A doubled flap 44 connects stack 35 to stack 34. The stack 34 is formed by folds around fold lines 38 from lateral portion 34a, shown in FIG. 1. Stack 35 and flap 44 are formed by folds around fold lines 36 from opposed lateral portion 35a. Fold lines 36 and 38 are preferably all parallel to lateral edges 28 and 29.

Stack 34, shown in FIG. 2, is formed by fan folding lateral portion 34a beginning with a forward fold around fold line 38a and followed by alternate reverse and forward folds around parallel fold lines (38b, 38c, 38d, . . . ) to create stacked panels of about equal size. In a preferred embodiment, the uppermost panel of stack 34 is reverse folded around fold line 38t so that lateral edge 28 is directed outwardly and is not even with the edge of stack 34 in order to make it easy to see and grasp.

The stack 35 and flap 44 are made from lateral portion 35a by first forming the flap 44, then fan folding the stack 35 on top of a portion of flap 44, and finally roll folding the rest of flap 44 atop the stack 35. To form flap 44, two panels are formed by a forward fold around fold line 36a followed by a reverse fold around fold line 36b, as shown in FIG. 3. The reverse fold around fold line 36b is followed by alternating forward and reverse folds for the remainder of portion 35a around parallel fold lines (36c, 36d, . . . ), creating panels of about equal size comprising stack 35. The lower panel of flap 44 is connected to stack 34 and the upper panel to stack 35, as shown in FIG. 3. The panels of stack 35 are preferably of a width less than half the width of the doubled portion of flap 44; the extension of flap 44 extends outwardly from under stack 35. The extension of flap 44 is roll folded atop stack 35 by a fold around fold line 36r, as shown in FIG. 4. In a preferred embodiment, the end of flap 44 is then roll folded in the opposite direction around fold line 36s forming flap panel 48 directed outwardly with its end not even with the edge of stack 35 in order to make it easy to see and grasp.

The laterally folded drape which results is then transversely folded. Transverse folding is shown in FIGS. 6-8 with the laterally folded drape, composed of stacks 34 and 35 and flap 44, shown as a single line in those figures. The formation of the pair of stacks 52 and 54 of transverse panels is accomplished by folding longitudinal portions 52a and 54a, FIG. 5, around fold lines 56 and 58, respectively. Fold lines 56 and 58 are parallel to longitudinal edges 26 and 27 and perpendicular to fold lines 36 and 38.

Stack 52, as shown in FIG. 6, is formed by fan folding longitudinal portion 52a beginning with a forward fold around fold line 56a and followed by alternate reverse and forward folds around parallel fold lines (56b, 56c, . . . ) to create stacked panels of about equal size.

The creation of stack 54 from opposed longitudinal portion 54a begins, as shown in FIG. 6, by reverse folding end panel 68 around fold line 58a. This creates looped end portion 70, which is subsequently forward folded around fold line 58b on top of stack 52 as shown in FIG. 7. A doubled loop 72, engulfing and extending away from stack 52, results which is then roll folded atop end panel 68 and stack 52, around fold line 58c, creating outside panel 74, inside panel 75 and outside panel 76 all of approximately equal size, as shown in FIG. 8. Panel 76 is the outward facing panel of stack 52. Panel 74 is the outward facing panel of stack 54.

A tape strip 77 is positioned on the folded drape, as shown in FIGS. 8 and 9, on outside panel 76. The tape strip 77 is preferably double-sided adhesive tape, one side of which secures the tape strip to the drape and the other side of which is covered by a release strip. The tape strip 77 can be positioned anywhere on panel 76 or panel 74, but is preferably placed as shown in FIG. 9, on panel 76 near the edge defined by fold line 36r.

Figure 10:
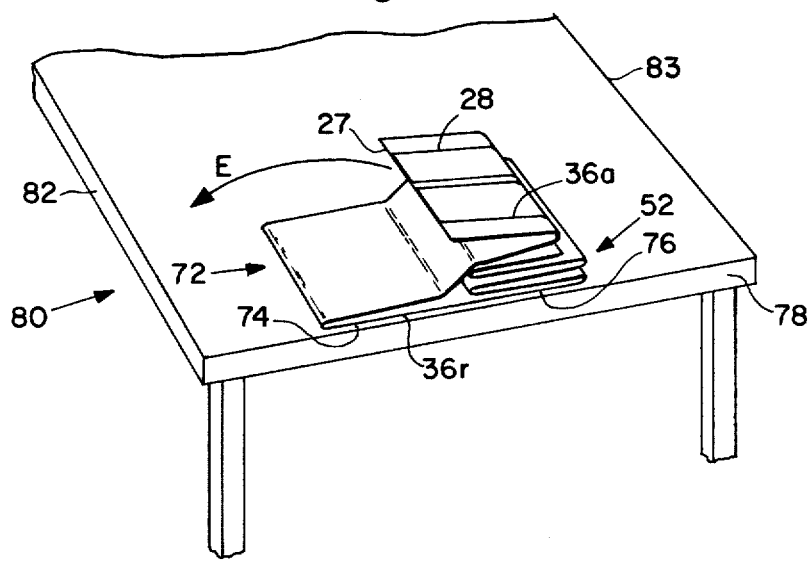
FIGS. 10 and 11 are fragmentary perspective views of the drape positioned on an overhead table and being unfolded.

To utilize the folded drape, the release strip covering the tape strip 77 is removed and the drape folded as shown in FIG. 8 is placed on table 80 medially along reference edge 78, with its lateral edges 28 and 29 positioned parallel to the reference edge 78 and fold line 36r of stack 35 positioned adjacent the reference edge. The drape is secured to the table by applying pressure to the top of the folded drape above the tape strip. Double fold 72 of transverse panels is folded down onto the table adjacent stack 52 by reversing the roll fold around fold line 58c, so that outside panels 74 and 76 rest on table 80 as shown in FIG. 10.

Figure 11:
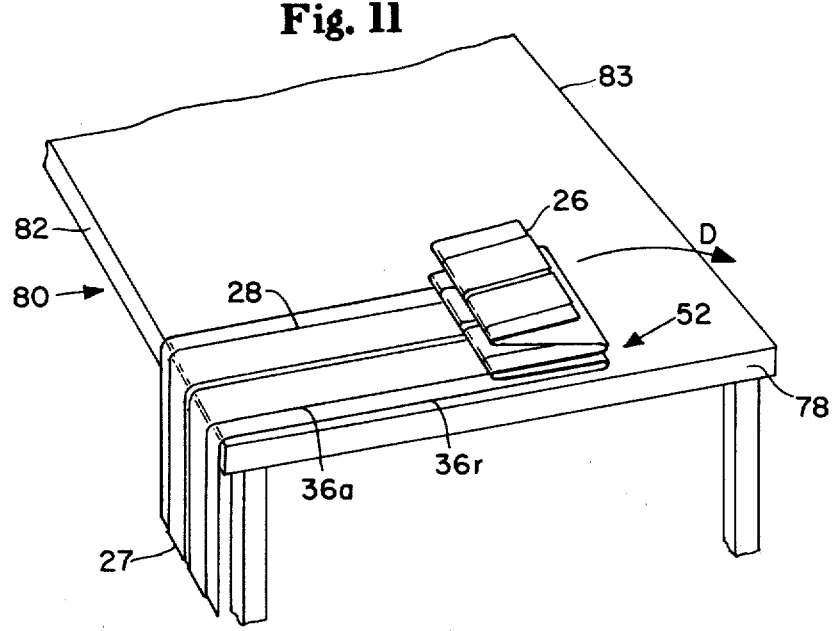

With exposed panels 74 and 76 against the table, the drape is now positioned for completion of unfolding by sterile personnel if desired. The draping nurse stands by the table adjacent and facing the reference edge 78 and completes the unfolding of stacks 54 and 52 of transverse panels. She grasps uncovered edge 27 between the thumb and forefinger of the left hand and unfolds stack 54 by pulling outwardly in the direction shown by the arrow E in FIG. 10 and by dropping it over the left edge 82 of table 80 as shown in FIG. 11. The nurse then grasps uncovered edge 26 between the thumb and forefinger of the right hand, and unfolds stack 52 and drops it over the right edge 83 of table 80 in the direction indicated by the arrow D in FIG. 11. The laterally folded drape extends about equidistantly over and well below side edges 82 and 83 of the table 80 as shown in FIG. 11.

Figure 12:
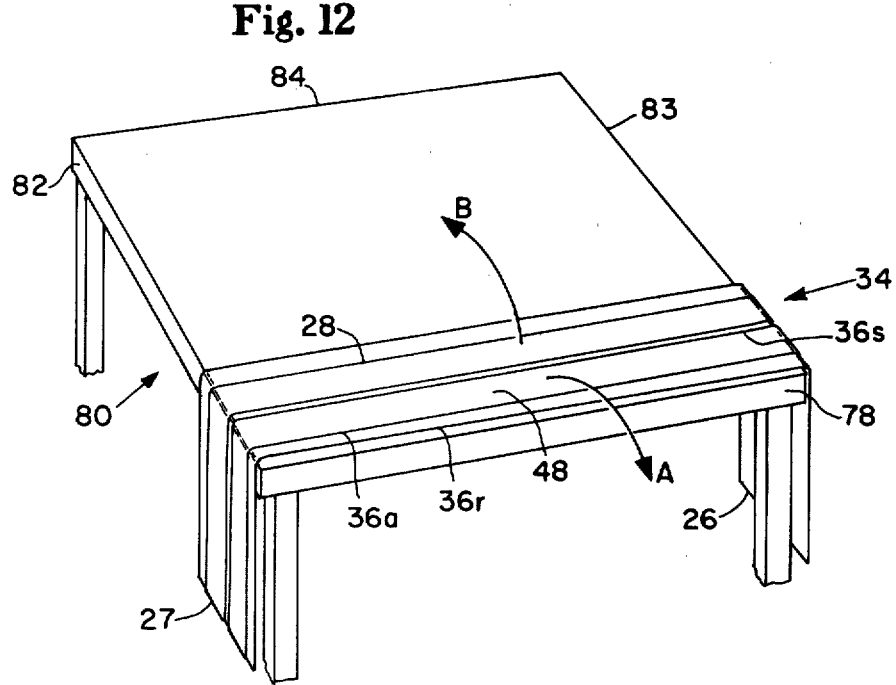
FIG. 12 shows a fragmentary perspective view of a drape positioned parallel to the reference edge of the table having been transversely unfolded and ready to be laterally unfolded.

The doubled flap 44, now exposed, is unfolded over reference edge 78 of the table by pulling towards the nurse as indicated by the arrow A in FIG. 12, causing the extension of flap 44 to hang down over the reference edge 78 secured in position by the lateral stacks 35 and 34. The flap 44 is conveniently handled by grasping flap panel 48 and pulling towards the nurse reversing the roll folds around fold lines 36s and 36r, and finally dropping the flap 44 over edge 78.

Figure 13:
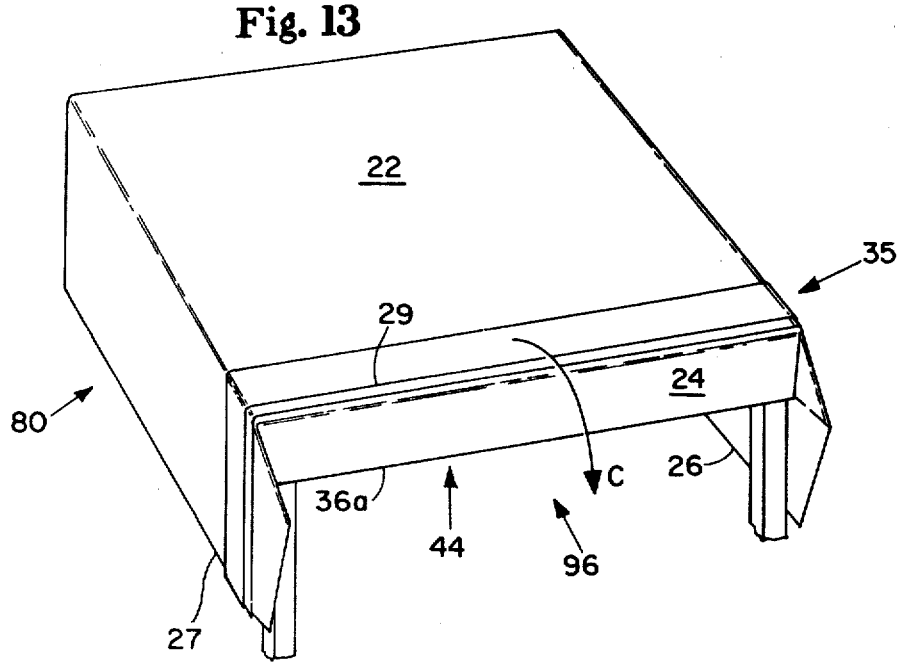
FIG. 13 is a fragmentary perspective view of the draped table ready to be positioned over a patient.

The stack 34 is then unfolded as indicated by the arrow B in FIG. 12, over the end 84 of the table 80 opposite the reference edge 78, covering side edges 82 and 83 as well, as shown in FIG. 13. The unfolding of stack 34 is conveniently accomplished by the nurse who grasps lateral edge 28 atop stack 34 between the thumb and forefinger of each hand, at spaced points along the edge 28, and moves it across table 80, dropping the edge 28 over end 84 with or without the assistance of a second nurse, depending on the size of table 80. The doubled flap 44 protects the nurse from contamination by the nonsterile reference edge 78 of the table during this process. Because the stack 35 of lateral panels is still positioned atop the table and only the extension of flap 44 extends over the reference edge, a tunnel 96 into the region below the table 80 is created between the fold line 36a of flap 44 and the floor.

Figure 14:
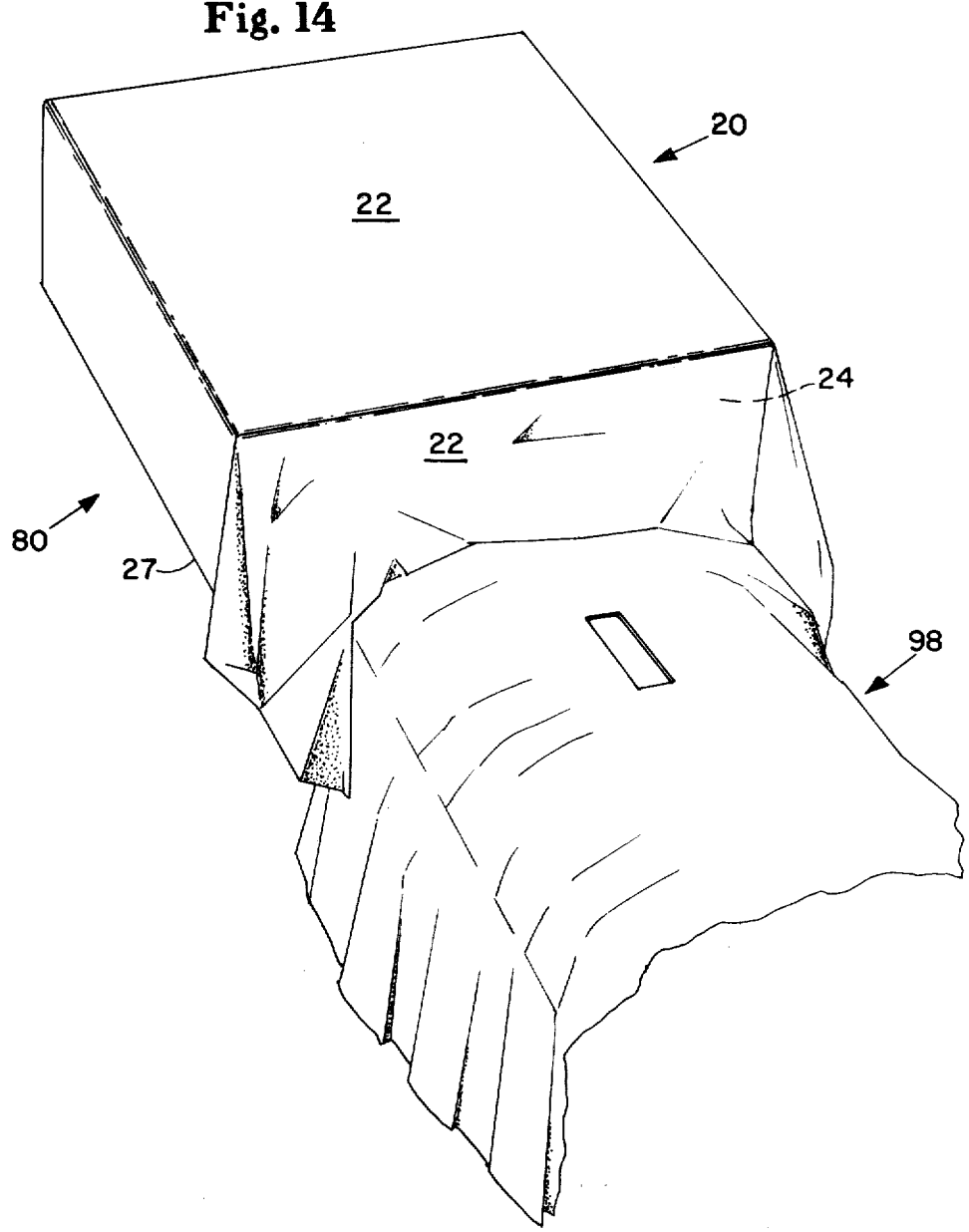
FIG. 14 is a fragmentary perspective view of the straddling-type table positioned over a patient with the drape completely unfolded.

The draped table 80 may then be positioned over the patient, reference edge 78 usually passing over the patient's feet first. Since the flap 44 does not extend as far below the reference edge 78 as the drape extends over the other edges of the table, this can be accomplished easily. Once the table is positioned with the reference edge 78 adjacent the operative site, the stack 35 and the flap 44 can be pulled down onto the patient 98 adjacent the operative site, as shown in FIG. 14. This is accomplished by pulling edge 29 which is atop stack 35 over reference edge 78 of the table as indicated by the arrow C in FIG. 13 so that most of lateral portion 35a extends below edge 78. The unfolded drape may extend further below reference edge 78 than it extends below the end 84 and edges 82.

Although the outward face of the extension of flap 44 may be contaminated as it passes over the patient, either by the patient or by the underside of the table as the table is being positioned, sterility is not compromised. This is because the contaminated outward face of the flap 44 extension is a portion of the lower side 24 of the drape 20, the upper side 22 surface being folded face-to-face. When the stack 35 is pulled down onto the patient 98, the contaminated side of the flap 44 is separated from the operative site by the flap itself. In this way sterility of draping nurse and operative site are protected from contamination developed in the course of table draping and positioning.

While particular embodiments of the present invention have been illustrated and described, it will be obvious to those skilled in the art that various changes and modifications can be made without departing from the spirit and scope of the invention. It is intended to cover, in the appended claims, all such modifications that are within the scope of this invention.

What is claimed is:

1. A folded, overhead table drape having an upper side and a lower side for contacting a table comprising:
(a) a first stack of panels folded around parallel fold lines having an uppermost panel, a lowermost panel, and two side edges parallel to said fold lines;
(b) a second stack of panels folded around parallel fold lines having an uppermost panel, a lowermost panel, and two side edges parallel to said fold lines; and
(c) a length of material integrally connected to a connecting panel of each of said first and second stacks, said length of material extending from said connecting panel of said first stack underneath said second stack to said connecting panel of said second stack, said length of material being folded such that it comprises a segment having adjacent surfaces, said segment of folded length of material being positioned such that it extends alongside at least a portion of one of said side edges of said second stack and atop the uppermost panel of at least said second stack.

2. The drape of claim 1 which is made of a thin sheet of polymeric film, a substantial portion of which is covered on its upper side by a nonwoven fabric.

3. The drape of claim 1 wherein said folded drape is folded into a second pair of stacks of panels around parallel fold lines perpendicular to the fold lines of said first mentioned pair of stacks of panels.

4. The folded drape of claim 3 wherein an adhesive fastener for securing said drape to a table is provided on the outside surface of one of said second pair of stacks of panels.

5. The folded drape of claim 1, 2 or 4 wherein exposed surfaces of said folded length of material consist of portions of said lower side of said drape.

6. The folded drape of claim 5 wherein said first stack of panels and said second stack of panels are juxtaposed stacks.

7. The folded drape of claim 6 wherein said juxtaposed stacks of panels are fan folded.

8. The folded drape of claim 7 wherein said connecting panels of said first and second stacks are said lowermost panels of said stacks.

9. The folded drape of claim 8 wherein said segment of folded length of material is doubled.

10. The folded drape of claim 7 wherein said segment of folded length of material is doubled.

11. The folded drape of claim 5 wherein said connecting panels of said first and second stacks are said lowermost panels of said stacks.

12. The folded drape of claim 5 wherein said segment of folded length of material is doubled.

13. The folded drape of claim 1 wherein said connecting panels of said first and second stacks are said lowermost panels of said stacks.

14. The folded drape of claim 1 wherein said segment of folded length of material is doubled.

* * * * *